United States Patent
Sun et al.

(10) Patent No.: US 10,849,724 B2
(45) Date of Patent: Dec. 1, 2020

(54) HIGH STRENGTH THREE DIMENSIONAL FABRICATING MATERIAL SYSTEMS AND METHODS FOR PRODUCING DENTAL PRODUCTS

(71) Applicant: DENTSPLY SIRONA Inc., York, PA (US)

(72) Inventors: Benjamin Jiemin Sun, York, PA (US); Andrew M. Lichkus, York, PA (US)

(73) Assignee: DENTSPLY SIRONA Inc., York, PA (US)

( * ) Notice: Subject to any disclaimer, the term of this patent is extended or adjusted under 35 U.S.C. 154(b) by 530 days.

(21) Appl. No.: 15/638,031

(22) Filed: Jun. 29, 2017

(65) Prior Publication Data

US 2018/0000570 A1    Jan. 4, 2018

Related U.S. Application Data

(60) Provisional application No. 62/356,711, filed on Jun. 30, 2016.

(51) Int. Cl.
| | |
|---|---|
| *B33Y 10/00* | (2015.01) |
| *A61C 13/00* | (2006.01) |
| *B29C 64/124* | (2017.01) |
| *B33Y 30/00* | (2015.01) |
| *B33Y 80/00* | (2015.01) |
| *B29C 64/245* | (2017.01) |

(Continued)

(52) U.S. Cl.
CPC ...... *A61C 13/0019* (2013.01); *A61C 13/0004* (2013.01); *A61C 13/0013* (2013.01); *A61C 13/01* (2013.01); *A61C 13/08* (2013.01); *B29C 64/124* (2017.08); *B29C 64/129* (2017.08); *B29C 64/245* (2017.08); *B33Y 10/00* (2014.12); *B33Y 30/00* (2014.12); *B33Y 80/00* (2014.12); *B29L 2031/7536* (2013.01)

(58) Field of Classification Search
CPC ....... B33Y 30/00; B33Y 80/00; B29C 64/245; B29C 64/129
USPC .......................................................... 264/18
See application file for complete search history.

(56) References Cited

U.S. PATENT DOCUMENTS

| | | |
|---|---|---|
| 5,059,266 A | 10/1991 | Yamane |
| 5,204,055 A | 4/1993 | Sachs |

(Continued)

FOREIGN PATENT DOCUMENTS

GB    2514139 A    11/2014

OTHER PUBLICATIONS

International Search Report; PCT/US2017/040166; Sep. 13, 2017 (completed); dated Sep. 25, 2017.

(Continued)

*Primary Examiner* — Jeffrey M Wollschlager
*Assistant Examiner* — Xue H Liu
(74) *Attorney, Agent, or Firm* — Dentsply Sirona Inc.

(57) ABSTRACT

This invention relates to printable high strength/toughness polymerizable material systems for making dental products such as artificial teeth, dentures, splints, veneers, inlays, onlays, orthodontic appliances, aligners, copings, frame patterns, crowns and bridges and the like. A DLP, stereolithography, modified or their modification and combination based printer is used to cure polymerizable material in several different methods of this invention to build-up the object. The resulting three-dimensional object has good dimensional stability.

17 Claims, 1 Drawing Sheet

(51) Int. Cl.
  *B29C 64/129* (2017.01)
  *A61C 13/01* (2006.01)
  *A61C 13/08* (2006.01)
  *B29L 31/00* (2006.01)

(56) References Cited

U.S. PATENT DOCUMENTS

| | | |
|---|---|---|
| 5,506,607 A | 4/1996 | Sanders |
| 5,740,051 A | 4/1998 | Sanders |
| 5,902,441 A | 5/1999 | Bredt |
| 6,270,335 B2 | 8/2001 | Leyden |
| 6,322,728 B1 | 11/2001 | Brodkin |
| 6,500,378 B1 | 12/2002 | Smith |
| 6,660,209 B2 | 12/2003 | Leyden |
| 6,921,500 B1 | 7/2005 | Feenstra |
| 6,939,489 B2 | 9/2005 | Moszner |
| 6,955,776 B1 | 10/2005 | Feenstra |
| 7,189,344 B2 | 3/2007 | Rheinberger |
| 2004/0094058 A1 | 5/2004 | Kasperchik |
| 2005/0082710 A1 | 4/2005 | Oriakhi |
| 2014/0131908 A1* | 5/2014 | Sun .............. A61K 6/083 264/16 |
| 2014/0167300 A1 | 6/2014 | Lee |

OTHER PUBLICATIONS

Written Opinion of the International Searching Authority; PCT/US2017/040166; Sep. 13, 2017 (completed); dated Sep. 25, 2017.
International Preliminary Report on Patentability; PCT/US2017/040166; Sep. 13, 2017 (completed); dated Sep. 25, 2017.

\* cited by examiner

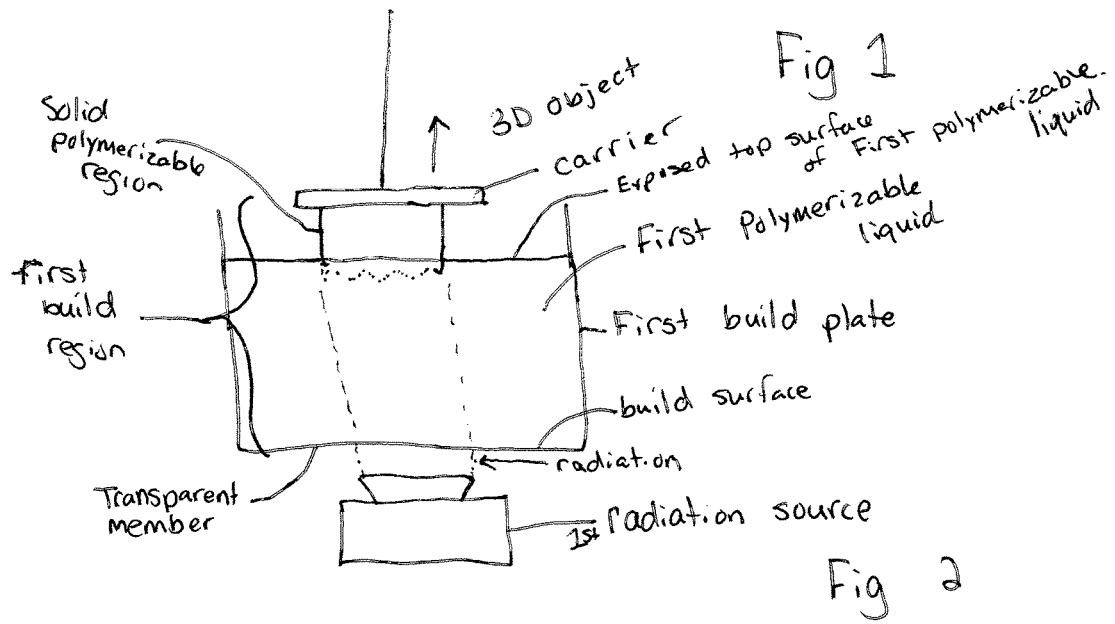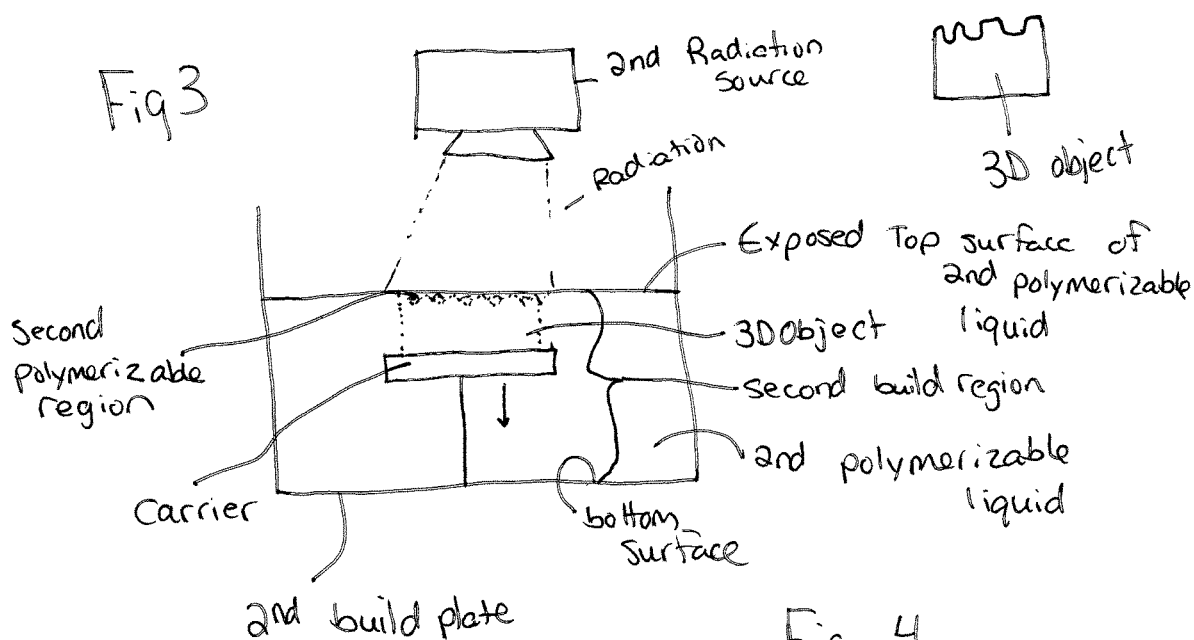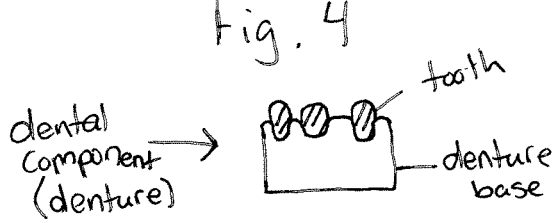

HIGH STRENGTH THREE DIMENSIONAL FABRICATING MATERIAL SYSTEMS AND METHODS FOR PRODUCING DENTAL PRODUCTS

THE CROSS-REFERENCE TO RELATED APPLICATIONS

This patent application claims the benefit of and priority to U.S. Provisional Patent Application Ser. No. 62/356,711, filed on Jun. 30, 2016, which is herein incorporated by reference for all purposes.

BACKGROUND

The present invention relates generally to rapid prototyping systems for making dental devices such as, for example, artificial teeth, dentures, splints, veneers, inlays, onlays, orthodontics, aligners, copings, frame patterns, crowns and bridges, models, appliances and the like. More particularly, using stereolithography or DLP (digital light projection) or other energy sources to build-up the dental devices as three-dimensional objects from novel high strength/toughness liquid resins of this invention. DLP system builds three-dimensional objects by using the Digital Light Processor (DLP) projector to project sequential voxel planes into liquid resin, which then caused the liquid resin to cure. SLA using laser beam traces out the shape of each layer and hardens the photosensitive resin in a vat (reservoir or bath).

In general, rapid prototyping refers to a conventional manufacturing process used to make parts, wherein the part is built on a layer-by-layer basis using layers of hardening material. Per this technology, the part to be manufactured is considered a series of discrete cross-sectional regions which, when combined together, make-up a three-dimensional structure. The building-up of a part layer-by-layer is very different than conventional machining technologies, where metal or plastic pieces are cut and drilled to a desired shape. In rapid prototyping technology, the parts are produced directly from computer-aided design (CAD) or other digital images. Software is used to slice the digital image into thin cross-sectional layers. Then, the part is constructed by placing layers of plastic or other hardening material on top of each other. There are many different techniques that can be used to combine the layers of structural material. A final curing step may be required to fully cure the layers of material.

Ink-jet printing technology is a rapid prototyping method that can be used to fabricate the three-dimensional object. In one well known ink-jet printing method that was developed at Massachusetts Institute of Technology, as described in Sachs et al., U.S. Pat. No. 5,204,055, printer heads are used to discharge a binder material onto a layer of powder particulate in a powder bed. The powdered layer corresponds to a digitally superposed section of the object that will be produced. The binder causes the powder particles to fuse together in selected areas. This results in a fused cross-sectional segment of the object being formed on the platform. The steps are repeated for each new layer until the desired object is achieved. In a final step, a laser beam scans the object causing the powdered layers to sinter and fuse together. In another ink-jet printing process, as described in Sanders, U.S. Pat. Nos. 5,506,607 and 5,740,051, a low-melting thermoplastic material is dispensed through one ink-jet printing head to form a three-dimensional object. A second ink-jet printer head dispenses wax material to form supports for the three-dimensional object. After the object has been produced, the wax supports are removed, and the object is finished as needed.

Leyden et al., U.S. Pat. Nos. 6,660,209 and 6,270,335 disclose an ink-jet printing method using commercial print heads having multiple orifices (jets) to selectively fire droplets of hot melt, radiation-curable material onto a substrate. Each orifice can be equipped with a piezoelectric element that causes a pressure wave to propagate through the material when electric current is applied. The print head moves along a scan path selectively depositing the flowable material onto the substrate. In a subsequent step, light radiation is used to cure the material.

Yamane et al., U.S. Pat. No. 5,059,266 discloses an ink-jetting method, whereby a photosetting or thermosetting resin is jetted along a flight passage of the material to a stage to thereby laminate the material on the stage, changing at least one of a jetting direction of the material along the flight passage and a jetting amount of the material, thereby controlling a jetting operation of the material, and exposing the laminated material to light to cure the material, thereby forming the article.

Bredt et al., U.S. Pat. No. 5,902,441 describes another ink-jet printing method, which involves applying a layer of powder particles containing an activatable adhesive onto a flat surface that can be indexed downward. The ink-jet printer introduces an activating fluid onto to the layer of particles in a predetermined pattern. The fluid activates the adhesive in the mixture, causing the particles to adhere together in an essentially solid layer. After the first cross-sectional portion of the article is formed, the movable surface can be indexed downward. Successive layers of the mixture of particles are applied in the same manner to form the desired article.

Oriakhi et al., US Patent Application Publication No. US 2005/0082710 discloses an ink-jet printing method, wherein a particulate blend of reactive glass ionomer particulates, cross-linkable polyacid particulates including polyvinyl pyrrolidone-co-polyacrylic acid, and nanocomposites is spread in a fabrication bin. An ink-jet printer applies an aqueous phase binder onto a predetermined area of the particulate blend to form hydrated cement. A glass-ionomer chemical reaction causes the hydrated cement to harden.

Kapserchik et al., US Patent Application Publication No. US 2004/0094058 discloses an ink-jet printing system using acid-base cements. Layers of powder particulate are deposited on a flat surface. The powders include a base such as a metal oxide or an aluminosilicate glass, a polymeric acid or other acid. The ink-jet printer dispenses an aqueous binder. The basic powder interacts with the acid in the presence of water, causing the formation of an ionically cross-linked hydrogel salt. Formation of the cross-linked hydrogel causes setting of the mixture.

More particularly, ink-jet printing methods for making three-dimensional dental products have been developed and are described in the patent literature.

For example, Moszner et al., U.S. Pat. No. 6,939,489 discloses a process for fabricating three-dimensional dental form pieces for dental restoration and replacement parts using three-dimensional plotting technology. The object is produced in a layered manner by the cutting away of micro drops or micro cords discharged from nozzles in the three-dimensional plotter. The discharged material can be hardened by a variety of mechanisms depending upon the type of material used. This includes cooling of melted material, polycondensation, polyaddition, or thermal-curing, and light radiation. In the '489 Patent, the three-dimensional plotting technology is described as being different than conventional rapid prototyping (selective laser sintering, 3D printing, and stereolithography).

Rheinberger et al., U.S. Pat. No. 7,189,344 discloses a process for producing three-dimensional dental restorative parts, such as full or partial dental prosthesis, using ink-jet printers that are used in the ink-jet printing methods developed by MIT as described above. The process involves spraying a polymerizable material onto a base support in a layer-by-layer manner. Each layer of material is polymerized by a light source prior to the application of the next layer. The polymerizable material is described as being wax-like having up to 70% by weight of at least one of a polymerizable monomer and oligomer; from 0.01 to 10% by weight of a polymerization initiator; and at least 20% by weight of a mixture having a selected one of a wax-like and flowable monomer and a color pigment.

Feenstra, U.S. Pat. Nos. 6,921,500 and 6,955,776 disclose an ink-jet printing process for making dental elements such as crowns using a liquid binder and powder bed. The element is produced by applying successive layers of powder and discharging the liquid binder onto the layers using an ink-jet printer. The binder preferably includes nanomeric, inorganic solid particles having polymerizable and/or polycondensable organic groups at their surface. After the binder has been applied to the last layer of powder, any excess, unbound powder is removed. Then, the powdered layers are sintered by heating to a temperature in the range of about 400 to 800° C. The sintering step is performed so that only necks between the powder particles are formed. The resulting sintered dental element is infiltrated by a second phase material, such as glass-ceramic or polymer, which melts at a lower temperature than the material of the dental element. This reduces the porosity of the dental element.

Bordkin et al., U.S. Pat. No. 6,322,728 discloses an ink-jet printing process for making dental restorations by printing a binder into layers of powder. The process involves depositing a layer of ceramic or composite powder material onto a powder bed. The design of the restoration is based on a CAD representation. A binding material is applied onto the ceramic or composite layer. This application of powder/binder material is repeated several times to produce the desired shape of the restoration. After the layering process is completed, the structure is cured to further promote binding of the particles.

The present invention provides novel high strength/toughness liquid resin systems for fabricating three-dimensional dental devices using the Digital Light Processor (DLP) projectors or stereolithography. Although the DLP method or stereolithography and high strength/toughness materials are described primarily herein as being used to make a splint, aligner, full and partial denture, denture base and artificial teeth, it should be understood that this is for illustration purposes only. The DLP method or stereolithography using high strength/toughness materials can be used to make any dental device such as, for example, artificial teeth, dentures, orthodontics, splints, veneers, inlays, onlays, copings, frame patterns, crowns and bridges and the like. We have provided a general description of these methods using high strength/toughness material systems as follows. (A more detailed description of the methods and high strength/toughness materials used to make the dental devices is set forth below.)

In this method, a polymerizable liquid resin material or heated resin material as a liquid is loaded into a resin bath of a 3D printer based on a DLP method, stereolithography or a combination of DLP and stereolithography. In the case of using DLP method, it builds 3D objects by projecting sequential voxel planes into liquid resin (or heated liquid resin), which then polymerizes it to solid. Successive layers of polymerized material are added in this manner until the device is completely fabricated. Multiple light (or laser) sources may be used with these methods. Once first object was built with successive layers of first polymerized materials, subsequent successive layers of second polymerized material may be added to first polymerized object by these methods. Similarly, additional polymerized materials can be built on above objects having two polymerized materials to form final device. Then the device, for example, a denture, is washed, finished and fully final cured as needed. The fully cured and polished denture is now ready to be used by the patient. In the case of aligner or splint, a clear vat of polymerizable liquid resin material might be used and built up the devices layer by layer.

SUMMARY OF THE INVENTION

In the present invention, several material systems and methods are used to manufacture the dental device. The high strength/toughness materials of this invention are suitable for dental application and cured to superior mechanical strength and have excellent physical properties. Further, these materials have good biocompatibility making it ideal for dental applications. The use of these unique high strength/toughness polymerizable materials by several novel 3D printing methods of this invention can easily prepare multiple shaded dental devices.

In one aspect, the present invention is directed to a method for forming a dental component, the method comprising the steps of (a) providing a carrier and a build plate, said build plate comprising a transparent member, said transparent member comprising a first build surface with said first build surface and said carrier defining a first build region therebetween; (b) filing said first build region with a first polymerizable liquid, said first polymerizable liquid contacting said first build surface; (c) irradiating said first build region through said build plate to produce a solid polymerized region from said first polymerizable liquid in said first build region; (d) advancing said carrier with said first polymerized region adhered thereto away from said first build surface on said build plate to create a subsequent first build region between said polymerized region and said first build surface; (e) repeating steps (c) and (d) to form a three-dimensional object having a first surface and a second surface adhered to said carrier, the first surface of the three-dimensional object between positioned between the first build surface and a second surface of the three-dimensional object; (f) filing a second build region with a second polymerization liquid, wherein an exposed top surface of the second polymerization liquid and a second build surface define the second build region therebetween; and wherein the second polymerizable liquid is different than the first polymerizable liquid; (g) repositioning the three-dimensional object so that the first surface of the three-dimensional object is positioned between the exposed top surface of the second polymerizable liquid and the second build surface; (h) irradiating the second build region to produce a second solid polymerized region from said second polymerizable liquid in said second build region; (i) advancing said carrier with the three-dimensional object and the said second polymerized region adhered the three-dimensional object away from said exposed top surface of the second polymerizable liquid to create a subsequent second build region between said second polymerized region and said second build surface; and (j) repeating steps (h) and (i) to form said three-dimensional dental component.

In another aspect, any of the aspects of the present invention may be further characterized by one or any combination of the following features: wherein the first surface of the three-dimensional object opposes the second surface of the three-dimensional surface; wherein the repositioning step (g), the carrier with the second surface adhered thereto is positioned between the second build surface and the first surface of the three-dimensional object; wherein the repositioning step (g), the three-dimensional object in rotated between 90 degrees and 270 degrees; further comprising the step of providing at least one radiation source for irradiation of steps (c) and/or (h); wherein the at least one radiation source includes a first radiation source such that the transparent member is provided between the first radiation source and the first build surface; wherein the transparent member is a semipermeable member; wherein the at least one radiation source includes a second radiation source such that the exposed surface of the second polymerizable liquid is provide between the second radiation source and the second build surface; wherein the at least one radiation source is movable from a first position such the transparent member is provided between the first radiation source and the first build surface and a second position such that the exposed surface of the second polymerizable liquid is provide between the second radiation source and the second build surface; wherein the at least one radiation source includes a first radiation source for irradiation of step (c) so that the transparent member is provided between the first radiation source and the first build surface and the at least one radiation source includes a second radiation source for the irradiation of step (h) such that the exposed surface of the second polymerizable liquid is provide between the second radiation source and the second build surface; wherein after step (e) and prior to step (f), remaining first polymerizable material is removed from the build plate; wherein the filling step (f), the build plate if filled with the second polymerizable material; further comprising the step of providing a second build plate, wherein the filling step (f), a second build plate is filled with the second polymerizable material; wherein the second build plate includes a bottom surface such that the carrier is advanced towards the bottom surface of the second build plate during step (i); wherein the repositioning step (g), the three-dimensional object in rotated between 135 degrees and 225 degrees; wherein the dental component is a denture and the first polymerized region forms part of a denture base of the denture; wherein the second polymerized region forms part of a tooth of the denture; the first polymerized region has a higher stress yield than the second polymerizable region; wherein the carrier is movable from a first position in contact with the exposed top surface of the first polymerizable liquid to a second position elevated above and without contact with the exposed top surface; wherein the carrier is movable from a third position within the second polymerizable liquid to a fourth position within the second polymerizable liquid further away from the exposed top surface of the second polymerizable liquid; or any combination thereof.

It should be appreciated that the above referenced aspects and examples are non-limiting as others exist with the present invention, as shown and described herein. For example, any of the above mentioned aspects or features of the invention may be combined to form other unique configurations, as described herein, demonstrated in the drawings, or otherwise.

BRIEF DESCRIPTION OF THE DRAWINGS

FIG. 1 is a perspective view of one embodiment of the present invention;

FIG. 2 is a perspective view of a three-dimensional object formed by a method using the embodiment of FIG. 1;

FIG. 3 is a perspective view of another embodiment of the present invention;

FIG. 4 is a perspective view of a three-dimensional dental component formed by a method using the embodiments of FIGS. 1-3.

DETAILED DESCRIPTION OF THE INVENTION

Printable Polymerizable Materials

A printable polymerizable material is used to make the dental products in accordance with the methods of this invention. By the term, "printable" as used herein, it is meant a material which is flowable (fluid) at a temperature below ambient temperature, at ambient temperature and above ambient temperature.

Flowable material having a flowable temperature in the range of −30° C. to 140° C. The following components can be used to prepare the printable polymerizable material in accordance with this invention.

Polymerizable Acrylic Compounds

Polymerizable acrylic compounds that can be used in the compositions of this invention, include, but are not limited to, mono-, di- or poly-acrylates and methacrylates such as methyl acrylate, methyl methacrylate, methacrylic acid, ethyl acrylate, ethyl methacrylate, isopropyl methacrylate, tert-butyl (meth)acrylate, cyclohexyl (meth)acrylate, 4-tert-butylcyclohexyl (meth)acrylate, tetrahydrofurfuryl (meth)acrylate, n-hexyl acrylate, 2-phenoxyethyl (meth)acrylate, stearyl acrylate, allyl acrylate, isobornyl (meth)acrylate, stearyl (meth)acrylate, phenoxy benzyl (meth)acrylate, o-phenylphenol ethyl (meth)acrylate, tris (2-hydroxy ethyl) isocyanurate diacrylate, the reaction product of octadecyl isocyanate and 2-hydroxyethyl methacrylate, the reaction product of octadecyl isocyanate and caprolactone 2-(methacryloyloxy)ethyl ester, the reaction product of octadecyl isocyanate and 2-hydroxyethyl acrylate; the reaction product of octadecyl isocyanate and hydroxypropyl (meth)acrylate; the reaction product of octadecyl isocyanate and 2-hydroxypropyl 2-(methacryloyloxy)-ethyl phthalate; the reaction product of octadecyl isocyanate and 2-hydroxy-3-phenoxypropyl acrylate; the reaction product of octadecyl isocyanate and glycerol dimethacrylate; the reaction product of octadecyl isocyanate and pentaerythritol triacrylate; the reaction product of cyclohexyl isocyanate and 2-hydroxyethyl (meth)acrylate; the reaction product of benzyl isocyanate and 2-hydroxyethyl (meth)acrylate; 1,14-tetradecanedimethacrylate, dimethylol tricyclodecane diacrylate, glycerol diacrylate, glycerol triacrylate, ethylene glycol diacrylate, diethyleneglycol diacrylate, triethyleneglycol dimethacrylate, tetraethylene glycol di(meth)acrylate, 1,3-propanediol diacrylate, 1,3-propanediol dimethacrylate, trimethylolpropane tri(meth)acrylate, 1,2,4-butanetriol trimethacrylate, 1,4-cyclohexanediol diacrylate, 1,4-cyclohexanediol dimethacrylate, 1,6-hexanediol di(meth)acrylate, pentaerythritol triacrylate, pentaerythritol tetraacrylate, pentaerythritol tetramethacrylate, sorbitol hexacrylate, 2,2-bis[4-(2-hydroxy-3-acryloyloxypropoxy)phenyl]propane; 2,2-bis[4-(2-hydroxy-3-methacryloyloxypropoxy)phenyl]propane (Bis-GMA); the reaction product of Bis-GMA and octadecyl isocyanate; the reaction product of Bis-GMA and cyclohexyl isocyanate; 2,2-bis[4-(acryloyloxy-ethoxy)phenyl]propane; 2,2-bis[4-(methacryloyloxy-ethoxy)phenyl]propane (or ethoxylated bisphenol A-dimethacrylate) (EBPADMA); urethane di(meth)acrylate (UDMA), diurethane dimethacrylate (DUDMA), 4,13-dioxo-3,14 dioxa-5,12-diazahexadecane-1,16-diol diacrylate; 4,13-dioxo-3,14 dioxa-5,12-diazahexadecane-1,16-diol dimethacrylate; 4,19-dioxo-3,20 dioxa-5, 18-diazahexadecane-1,22-diol diacrylate; 4,19-dioxo-3,20 dioxa-5,18-diazahexadecane-1,22-diol dimethacrylate; the reaction product of trimethyl 1,6-diisocyanatohexane and bisphenol A propoxylate and 2-hydroxyethyl methacrylate (TBDMA); the reaction product of 1,6 diisocyanatohexane and 2-hydroxyethyl methacrylate modified with water (HDIDMA); the reaction product of 1,6 diisocyanatohexane and 2-hydroxyethyl acrylate modified with water (HDIDA); the reaction product of 1,6-diisocyanatohexane, 1,2-decanediol, 1,10-decanediol and 2-hydroxyethyl (meth)acrylate; the reaction product of 1,6-diisocyanatohexane, 3-hydroxy 2,2-dimethylpropyl 3-hydroxy-2,2-dimethyl propionate, 1,10-decanediol and 2-hydroxyethyl (meth)acrylate; the reaction product of 1,6-diisocyanatohexane, 1,10-decanediol and 2-hydroxyethyl (meth)acrylate; the reaction product of 1,6-diisocyanatohexane, 1,2-decanediol, 1,10-decanediol, 3-hydroxy 2,2-dimethylpropyl 3-hydroxy-2,2-dimethyl propionate and 2-hydroxyethyl (meth)acrylate; the reaction product of 1,6-diisocyanatohexane, trimethyl 1,6-diisocyanatohexane, 1,10-decanediol and 2-hydroxyethyl (meth)acrylate; the reaction product of 1,6-diisocyanatohexane, trimethyl 1,6-diisocyanatohexane, 3-hydroxy 2,2-dimethylpropyl 3-hydroxy-2,2-dimethyl propionate, 1,10-decanediol and 2-hydroxyethyl (meth)acrylate; the reaction product of 1,6-diisocyanatohexane, 2,5-dimethyl-2,5-hexanediol and 2-hydroxyethyl (meth)acrylate; the reaction product of 1,6-diisocyanatohexane, 4,4'-isopropylidenedicyclohexanol and 2-hydroxyethyl (meth)acrylate; the reaction product of 1,6-diisocyanatohexane, 1,2-decanediol, 1,10-decanediol, 3-hydroxy 2,2-dimethylpropyl 3-hydroxy-2,2-dimethyl propionate and 2-hydroxyethyl (meth)acrylate; the reaction products of 2-isocyanatoethyl methacrylate and diols; polyurethane dimethacrylate (PUDMA); alkoxylated pentaerythritol tetraacrylate; polycarbonate dimethacrylate (PCDMA); the bis-acrylates and bis-methacrylates of polyethylene glycols; (meth)acrylate modified silicones; light curable epoxides; epoxy methacrylate (or acrylate), methacrylate (or acrylate) compounds or their combinations; various epoxides in combination with various diols [such as 1,3-bis(3-glycidyloxypropyl)tetramethyldisoxane, bisphenol A proxylate dig lycidyl ether, bis(3,4-epoxy-6-methylcyclohexylmethyl)adipate, 1,10 decanediol, 1,6-hexanediol, branched diol, aromatic diol, bisphenol A, proxylated bisphenol A, etc. Epoxy compounds polymerized by ring-opening polymerization shrinks less due to the increase in excluded free-volume associated with the ring-opening process in addition to the volume expansion from the phase conversion]; and copolymerizable mixtures of acrylated monomers and acrylated oligomers, and the like. For example, the use of rubber impact modifier in the 3D printing resin systems of this invention significantly increased the fracture toughness of formulated resin systems. The use of ethyl methacrylate to replace methyl methacrylate also significantly increased the fracture toughness of formulated 3D printing resin systems. However, the use of ethyl methacrylate to replace methyl methacrylate reduced the flexural strength and modulus of corresponded resin.

Polymerization System

The high strength/toughness printable polymerizable dental materials and compositions of this invention may include one or more initiating systems to cause them to harden promptly. Light polymerizable dental compositions or composites preferably include a light sensitizer, for example camphorquinone, 2,4,6-trimethylbenzoyldiphenylphosphine oxide, or methyl benzoin which causes polymerization to be initiated upon exposure to activating wavelengths of light; and/or a reducing compound, for example tertiary amine.

In one embodiment, a photoactive agent such as, for example, benzophenone, benzoin and their derivatives, or alpha-diketones and their derivatives is added to the composition in order to make it light-curable. A preferred photopolymerization initiator is camphorquinone (CQ). Cationic polymerization initiators, diaryliodonium and triaryl sulfonium salts, such as 4-octyloxy-phenyl-phenyl iodonium hexafluoroantimonate (OPPI), can also be used, which initiates ring opening polymerization as well as volume expansion from phase change to reduce the polymerization shrinkage. Electron-transfer photosensitizers, such as polynuclear aromatic compounds, their substituted analogues, carbazoles, phenothiazines, curcumin, and titanium-complex free radical initiator can also be added. In addition, various UV light initiators can also be used. Photopolymerization can be initiated by irradiating the composition with blue, visible light preferably having a wavelength in the range of about 400 to about 500 nm. A standard dental blue light-curing unit can be used to irradiate the composition. The camphorquinone (CQ) compounds have a light absorbency maximum of between about 400 to about 500 nm and generate free radicals for polymerization when irradiated with light having a wavelength in this range. Photoinitiators selected from the class of acylphosphine oxides can also be used. These compounds include, for example, monoacyl phosphine oxide derivatives, bisacyl phosphine oxide derivatives, and triacyl phosphine oxide derivatives. For example, 2,4,6-trimethylbenzoyl-diphenyl-phosphine oxide (TPO) can be used as the photopolymerization initiator.

In addition to the photoactive agents, the material of this invention may include a polymerization inhibitor such as, for example, butylated hydroxytoluene (BHT); hydroquinone; hydroquinone monomethyl ether; benzoquinone; chloranil; phenol; butyl hydroxyanaline (BHA); tertiary butyl hydroquinone (TBHQ); tocopherol (Vitamin E); and the like. Preferably, butylated hydroxytoluene (BHT) is used as the polymerization inhibitor. The polymerization inhibitors act as scavengers to trap free radicals in the composition and to extend the material's shelf life.

In one embodiment, a material referred to as "ALF" comprising camphorquinone (CQ); butylated hydroxytoluene (BHT); N, N-dimethylaminoneopentyl acrylate, gamma-methacryloxypropyl trimethoxy silane and methacrylic acid can be used in the composition.

Fillers

Conventional filler materials such as inorganic fillers, which can be naturally-occurring or synthetic, can be added to the printable polymerizable dental material and composition. Such materials include, but are not limited to, silica, titanium dioxide, iron oxides, silicon nitrides, glasses such as calcium, lead, lithium, cerium, tin, zirconium, strontium, barium, and aluminum-based glasses, borosilicate glasses, strontium borosilicate, barium silicate, lithium silicate, lithium alumina silicate, kaolin, quartz, and talc. Preferably, the silica is in the form of silanized fumed silica. Preferred glass fillers are silanized barium boron aluminosilicate and silanized fluoride barium boron aluminosilicate. Preferably, these surface treated inorganic fillers can be suspended in printable polymerizable resin. Most preferably, they form a homogeneous mixture. Organic particles such as poly(methyl methacrylate) (PMMA), highly crosslinked PMMA beads, poly(methyl/ethyl methacrylate), poly(methyl/butyl methacrylate), rubber modified PMMAs, rubber impact modifiers, crosslinked polyacrylates, thermoplastic and crosslinked polyurethanes, grounded polymerized compounds of this invention, polyethylene, polypropylene, polycarbonates and polyepoxides, and the like also can be used as fillers. These organic fillers can be added into printable polymerizable resin described above. Preferably, these organic fillers can dissolve or suspend in printable polymerizable resin. Most preferably, they form homogeneous colloids. Composite fillers, such as polymerized dental composites can be grounded and used in the formulations of this invention. Nanoparticles, fine glass particles, or other inorganic impregnated/modified PMMA or crosslinked polymer beads/particles from syntheses or grounding, surface treated or not, can also be used. These composite fillers can be selected based on specific printing resin systems for best compatibility and best bonding.

The inorganic filler particles can also be surface-treated with a silane compound or other coupling agent to improve bonding between the particles and resin matrix. Suitable silane compounds include, but are not limited to, gamma-methacryloxypropyltrimethoxysilane, gamma-mercaptopropyltriethoxysilane, gamma-aminopropyltrimethoxysilane, and combinations thereof.

Pigments

Printable polymerizable pigmented high strength/toughness materials of this invention contain one or more pigments as coloring or shading agents. The pigments include inorganic pigments and organic pigments. The pigments may be modified to increase the dispersibility. For example, modified pigments having a silane group, a polymerizable silane group, dialkylaminomethyl group or dialkylaminoethylsulfonic acid group are preferred used. In an additional example, inorganic pigments can be surface-treated with a silane compound, other coupling agent, surfactant or polymer to improve bonding between the particles and resin matrix as well as to enhance the dispersion in printable materials. Suitable silane compounds include, but are not limited to, gamma-methacryloxypropyltrimethoxysilane, gamma-mercaptopropyltriethoxysilane, gamma-aminopropyltrimethoxysilane, and combinations thereof. Many methods, including several mechanical methods, ultrasonic dispersing method, etc. may be used to disperse pigments into resin matrix of this invention.

Examples of the inorganic pigment include, but not limited to, black iron oxide, yellow iron oxide, ultramarine blue, brown iron oxide, titanium oxide, zinc flower, zinc oxide, iron oxide, aluminum oxide, silicone dioxide, talc, barium sulfate, calcium sulfate, red oxide, cobalt chrome green, Armenian blue, carbon black, mica, cobalt violet, molybdenum red, titanium cobalt green, molybdate orange, etc. Examples of the organic pigments include Cromophtal Red-BRN 2-napthalenecarboxamide, azo pigments, polyazo pigments, azomethine pigments, isoindoline pigments, anthraquinone pigments, phthalocyanine pigments, benzimidazolone pigments, etc. More important, a PMMA based pigments systems can be developed by encapsulating various pigments in fine PMMA polymer beads and form core shell structures, where pigment particles are encased in PMMA polymer beads, which are stable in resin matrix, especially MMA based high strength/toughness polymerizable liquid. Resin based pigment systems can also be developed by encapsulating various pigments in fine polymerized resin beads. These polymer beads can be prepared by emulsion or suspension polymerizations. Alternatively, high pigment concentrated resins or MMA based resins can be polymerized and then grounded into fine powders and subsequently used in polymerizable liquids to form colloids or desirable suspensions.

Pigmented materials are desirable because they have superior shade stability and stand up to UV light irradiation. This invention overcame the potential pigment separation from dental resins by dispersing the particles in the solution better to prevent settling and by milling the particles to smaller sizes. Mechanical methods were also applied to finely dispersed pigments in selected matrix, and polymeric additives so as to effectively stabilize and suspense pigments in liquid. This invention further overcame the potential pigment separation from dental resins by using nano-dispersed and fine inorganic and organic pigments. Nano-dispersed organic pigments are preferred to be used here.

The term "pigment" refers to visible materials which are not soluble, but are suspended or dispersed as fine particles in the subject materials. The preferred solid pigments are those pigments with fine particles, such as Black Iron Oxide 7053, Yellow Iron Oxide 7055, Titanium Dioxide, Cromophtal Red-BRN 2-napthalenecarboxamide, N,N'-(2-chloro-1,4-phenylene) bis{4-{(2,5-dichlorophenyl) azo}-3-hydroxy-}, ultramarine blue and brown iron oxide 420. In addition, a fluorescing agent may be included, such as Lumilux Blue LZ fluorescing agent (dihydroxy terepthalate acid ester). The polymerizable high strength/toughness materials of this invention utilize pigments having small particle sizes, which are better suspended in liquid vat. Although the pigment particles would tend to settle out of liquid vat, the compatible nature of our invented polymerizable materials with pigments prevents this potential separation during use at ambient or elevated temperature. The surface of pigments may be organically modified to improve its compatibility to resin or MMA based matrix.

Printable polymerizable high strength/toughness dental materials compositions of the invention may include various inorganic and organic fillers, pigments, initiators, catalysts, stabilizers, various modifiers, surfactants, antimicrobial agents, UV absorbing additives, thixotroping agents, plasticizers, impact modifiers, antifungal agents, fibers or their combinations. Preferred stabilizers are butylated hydroxytoluene (BHT) and the methyl ether of hydroquinone (MEHQ), etc. It may also include compounds to introduce radiopaque in the material.

Printable polymerizable high strength/toughness dental materials of the invention are able to rapidly solidify upon light irradiation.

Methods

3D Printing Using DLP System, Stereolithography or Similar Light Irradiation as Well as their Combinations In general, these two general approaches (DLP-type printer or Stereolithography-type printer) can be used for fabricating the three-dimensional object using the high strength/toughness materials of this invention. However, additional methods based on other light irradiation methods as well as the combination of DLP, stereolithography or other light irradiation methods may also be used. It is preferable a 3D printer for fabricating the three-dimensional object using multiple DLP light sources at different angles, laser beams or similar light irradiations from different angles or their combinations of different light sources from different angles. More preferable, light beams (or lasers) are able to irradiate 360 degree around the objects with light beams (or lasers) from horizontal to vertical directions. It is also preferable, light beams (or lasers) are able to move 360 degree around the objects with light beams (or lasers) irradiated from 360 degree from horizontal to vertical directions. It is also preferable, light beams (or lasers) are able to sense or/and adjust vertical position or beam direction based on the liquid resin level in vat with light beams (or lasers) irradiated from 360 degree around the objects from horizontal to vertical directions.

The printable polymerizable material is flowable or heated to form a flowable liquid prior to polymerization. Following each of these approaches of this invention, the printer builds successive layers of the polymerizable materials by projecting or irradiating light onto the building plane and cures to form the denture or other dental devices. The resulting denture or other dental devices built from these high strength/toughness materials of this invention should exhibit excellent mechanical and physical properties, various shade and color properties. Multiple shaded denture or other dental devices can be built from multiple shaded polymerizable materials in multiple vats.

Several printable polymerizable high strength/toughness materials with different shades and color can be prepared and placed into separate baths. In a case of build a denture, denture base is to build from denture base shaded bath layer by layer. This denture base is washed and transferred into a tooth dentin shaded bath to build tooth dentin part of denture teeth on denture base layer by layer, where light beams were irradiated from different angles (might be movable up to 360 degree and might irradiate from up to 360 degree from horizontal to vertical directions) so as to allow the layer by layer built up on the surface of first shaded denture base. Multiple light sources (or beams) as well as different light sources (or beams) may be used in a single printing unit. If desired, this can be washed and transferred into another dentin shaded bath to build additional dentin layer on the surface of previous built shapes. After it is washed and transferred into an enamel bath, where an enamel layer is built layer by layer on the surface of previous built shapes and forms a final denture device with integral teeth on denture base. If additional shades are desired, additional layers of different dentin and enamel shades or denture base and characterized denture base shades can be built similarly as described above. Nevertheless, a denture may be built by reversal steps, where teeth or enamel are built first and then denture base.

In addition to commonly used layer by layer method to build 3D objects, a time wise, intensity wise or combination of time and intensity wise method can also be used to control the depth of cure so as to control 3D geometry, which allows a faster and more efficient way to build 3D objects. A time wise method means different spots (dots) having light irradiation applied at different length of time based on the different shades and curing depth requirements, so the different depth of cure is achieved at different spots according to the design to obtain various shapes and gradients. A intensity wise method means different spots (dots) having different light intensity applied based on different shades and curing depth requirements, so different depth of cure is achieved at different spots according to the design to obtain various shapes and gradients. A time or/and intensity wise method means different spots (dots) having different light intensity applied at different length of time based on different shades and curing depth requirements, so different depth of cure is more efficiently achieved at different spots according to the design to obtain various shapes and gradients. For different spots, different light intensity or/and irradiation time may be applied so varied thickness layers will be built at different spots. This method allows build a layer of different shaded material with different thickness on top (the surface) of prefabricated objects. It is preferable a printing process combines a layer by layer and time or/and intensity wise methods to be used to fabricate 3D objects. More specifically, a denture can be fabricated by combining a layer by layer method and time or/and intensity wise method. Denture base can be built in a vat of denture base liquid using a 3D printing based on light irradiation layer by layer. After removed and washed, this denture base can be inserted into a second vat containing dentin shaded liquid. A time or/and intensity wise method, a layer by layer method or their combination method is subsequently applied to this denture base to build tooth base layer with varied thickness. Subsequently layers may be built layerwisely (layer by layer), time or/and intensity wisely or their combination wisely. If additional shaded dentin is desired, this denture can be removed and washed, and then can be inserted into a third vat containing different dentin shaded liquid. A time or/and intensity wise method, a layer by layer method or their combination method is subsequently applied to this denture base for first layer to build tooth base layer with varied thickness and subsequently layers may be built layerwisely, time or/and intensity wisely, or their combination wisely. If additional shades are desired, this denture can be removed and washed, and then can be inserted into a fourth vat containing enamel shaded liquid. A time or/and intensity wise method is subsequently applied to this denture base for first layer to build tooth enamel layer with varied thickness and subsequently layers may be built layerwisely, time or/and intensity wisely or their combination wisely. Additional dentin and enamel shades can be built similarly as described above. Nevertheless, a denture may be built by reversal steps, where teeth or enamel are built first and then denture base.

In a case of mass production of denture teeth, multiple teeth can be built by first forming multiple neck parts of denture teeth in neck resin bath, and adding body parts of denture teeth in body resin bath, finally building enamel parts of denture teeth in enamel resin bath and final cure to form multiple denture teeth. Nevertheless, reversal steps may be used to build denture teeth with enamel layer built first. Multiple baths at ambient atmosphere or elevated temperature may be used as desired to build multiple shades and to achieve the desirable esthetics of formed dental devices. A layer by layer method, a time or/and intensity wise methods or their combinations may be used to build these denture teeth.

In a case of mass production of provisional or long term crowns and bridges, multiple crowns and bridges can be built by first forming multiple dentin parts of crowns and bridges in opaceous dentin resin bath, and dentin resin bath, finally building enamel parts of crowns and bridges in enamel resin bath and final cure to form multiple crowns and bridges. Nevertheless, reversal steps may be used to build crowns and bridges with enamel layer built first. Multiple baths at ambient atmosphere or elevated temperature may be used as desired to build multiple shades and to achieve the desirable esthetics of formed dental devices. A layer by layer method, a time or/and intensity wise methods or their combinations may be used to build these crowns and bridges.

In the case of fabrication of orthodontic aligner, a single bath will be used. A layer by layer method, a time or/and intensity wise method or their combination may also be used to build this aligner. A time or/and intensity-wise methods or the combinations with layer by layer method may offer faster build speed.

Preferably, high strength/toughness dental products are produced by the methods of this invention. In a preferred embodiment, the printable polymerizable high strength/toughness material (with no reinforcing fillers) can be cured from printer to produce the high-strength dental product. By the term, "high-strength" as used herein, it is meant that the products have a flexural modulus of at least 200,000 psi, a flexural strength of at least 5,000 psi, or maximum stress intensity factor $K_{max}$ of at least 1.0 MPa*m$^{1/2}$ and total fracture work $W_f$ at least 300 J/m$^2$. More preferably, the product has a flexural modulus of at least 300,000 psi, a flexural strength of at least 8,000 psi, or maximum stress intensity factor $K_{max}$ of at least 1.9 MPa*m$^{1/2}$ and total fracture work $W_f$ of at least 900 J/m$^2$. Most preferably, the product has a flexural modulus of at least 350,000 psi, a flexural strength of at least 12,000 psi, or maximum stress intensity factor $K_{max}$ of at least 2.2 MPa*m$^{1/2}$ and total fracture work $W_f$ of at least 1200 J/m$^2$. "Flexural strength, and flexural modulus" as used herein refers to properties measured according to the methods of ASTM D790 (1997). Maximum stress intensity factor $K_{max}$ and total fracture work $W_f$ as used herein refers to properties measured according to the methods of ISO20795-1 (2012).

As described in the following examples, various formulations of the printable polymerizable high strength/toughness materials can be prepared for use in a 3D printing device. It is important that the formulations have sufficiently low viscosity so that they can be handled easily and cured device can be removed easily from the liquid resin bath (reservoir or vat). At the same time, the formulations must be biocompatible, capable of producing dental products having sufficient mechanical strength and integrity. Several flowable, printable polymerizable high strength/toughness materials were prepared with various shades for different applications. The flowable, printable polymerizable high strength/toughness materials were successfully, locally cured to form various 3D objects. Several selected examples are shown in the Example Section. The materials of this invention were cured in this manner layer by layer, a time or/and intensity wisely or their combinations and formed 3D dental objects that can be separated from the rest of liquid resin in the bath of 3D printer. Additionally, wash solvents (e.g., ethyl acetate, alcohols, acetone, THF, heptane, etc. or their combinations) may be used to remove uncured resin from 3D dental objects and finally cured. A heat treatment may be used to enhance their mechanical and physical properties as well as their performance. Air barrier coating, sealer or high strength/toughness sealer of this invention may be used prior to final cure. Inert atmosphere in an enclosed building chamber or inert gas blanket may be used for final cure of dental devices or the mass production of dental devices (e.g., denture teeth, denture bases, crowns and bridges, splints, orthodontic appliances, aligners, etc.) in a manufacturing environment.

Alternatively, the materials of this invention can be made by other means to build 3D objects. In addition, the resin systems developed in this invention can be used in other industries, such as aerospace, animation and entertainment, architecture and art, automotive, consumer goods and packaging, education, electronics, hearing aids, sporting goods, jewelry, medical, manufacturing, etc.

EXAMPLES

Example 1

Preparation of Oligomer

A reactor was charged with 1176 grams of trimethyl-1,6-diisocyanatohexane (5.59 mol) and 1064 grams of bisphenol A propoxylate (3.09 mol) under dry nitrogen flow and heated to about 65° C. under positive nitrogen pressure. To this reaction mixture, 10 drops of catalyst dibutyltin dilaurate were added. The temperature of the reaction mixture was maintained between 65° C. and 140° C. for about 70 minutes and followed by additional 10 drops of catalyst dibutyltin dilaurate. A viscous paste-like isocyanate end-capped intermediate product was formed and stirred for 100 minutes. To this intermediate product, 662 grams (5.09 mol) of 2-hydroxyethyl methacrylate and 7.0 grams of BHT as an inhibitor were added over a period of 70 minutes while the reaction temperature was maintained between 68° C. and 90° C. After about five hours stirring under 70° C., the heat was turned off, and oligomer was collected from the reactor as semi-translucent flexible solid and stored in a dry atmosphere.

Example 2

Preparation of Urethane Monomer (UCDPMAA)

A 500 mL flask was charged with 38.8 grams (0.200 mol) of 1,3-bis(isocyanatomethyl)cyclohexane under dry nitrogen flow and heated to about 60° C. under positive nitrogen pressure. To this reaction mixture, 3 drops of catalyst dibutyltin dilaurate were added. A mixture of 22.7 grams of 2-hydroxy-3-phenoxy propyl acrylate, 26.6 grams (0.204 mol) of 2-hydroxyethyl methacrylate, 11.5 grams (0.099 mol) of 2-hydroxyethyl acrylate and 0.10 grams of BHT as an inhibitor were added over a period of 70 minutes while the reaction temperature was maintained between 56° C. and 78° C. After about four hours stirring, the heat was turned off, and monomer was collected from the flask as viscous liquid and stored in a dry atmosphere.

Example 3

Organic Filler Material

A polymerizable dental material was prepared by stirring at 85° C. a liquid mixture of 30.65 grams of oligomer made following the procedure of Example 1; 20 grams of the compound of Example 2; 40 grams of methyl methacrylate; 9 grams of rubber impact modifier S2006 (from Mitsubishi Rayon Co.); and 0.35 grams of 2,4,6-trimethylbenzoyldiphenylphosphine oxide, (Lucirin TPO made by BASF). This material was light cured and subsequently ground to form particulate powder containing particles having an average particle size in the range of about 1 to about 150 micrometers. Alternatively, these polymer beads can be made by suspension or emulsion polymerizations.

Example 4

Composite Filler Material

A polymerizable dental composite material was prepared by stirring at 85° C. a liquid mixture of 5.65 grams of oligomer made following the procedure of Example 1; 12.0 grams of the compound of Example 2; 6.0 grams of triethylene glycol dimethacrylate; 62 grams of silanated barium aluminoflurosilicate glass particles BAFG having an average particle size of from about 0.1 to about 1.5 micrometer; 14 grams of silanated barium aluminoflurosilicate glass particles BAFG having an average particle size of from about 1 to about 10 micrometers; 0.10 grams of 2,4,6-trimethylbenzoyldiphenylphosphine oxide, (Lucirin TPO made by BASF), and 0.25 grams of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane. This material was light cured and subsequently ground to form particulate powder containing particles having an average particle size in the range of about 1 to about 150 micrometers. Alternatively, these composite beads can be made by suspension or emulsion polymerizations.

Printable Polymerizable Compositions

Printable polymerizable compositions are used in a 3D building resin bath of 3D printer to fabricate the dental objects. These compositions may contain acrylate or methacrylate monomers or oligomers, polymers, fillers, catalysts, various modifiers, antimicrobial agents, UV absorbing additives, thixotroping agents, plasticizers, antifungal agents, fibers, impact modifiers, pigments, stabilizers and light curable initiators, etc. Preferably, these resins will form flowable liquids at ambient or elevated temperatures and cure rapidly at those temperatures required for different resins to form 3D objects using the methods disclosed in this invention. This results in shape-stable three-dimensional objects being formed immediately.

Example 5

Dental Materials

A polymerizable dental material was prepared by stirring at ambient temperature a liquid mixture of 35 grams of oligomer made following the procedure of Example 1; 46 grams of methyl methacrylate (MMA); 10 grams of 2-phenoxyethyl acrylate (SR339 from Sartomer); 7.5 grams of rubber impact modifier S2006 (from Mitsubishi Rayon Co.); 0.5 grams of 2,4,6-trimethylbenzoyldiphenylphosphine oxide, (Lucirin TPO available from BASF); and 1.0 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 6

Dental Materials

A polymerizable dental material was prepared by stirring at ambient temperature a liquid mixture of 35 grams of oligomer made following the procedure of Example 1; 48.5 grams of methyl methacrylate (MMA); 5 grams of Genomer 4256 (from Rahn); 10.0 grams of rubber impact modifier S2006 (from Mitsubishi Rayon Co.); 0.5 grams of 2,4,6-trimethylbenzoyldiphenylphosphine oxide, (Lucirin TPO available from BASF); and 1.0 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 7

Dental Materials

A polymerizable dental material was prepared by stirring at ambient temperature a liquid mixture of 35 grams of oligomer made following the procedure of Example 1; 30 grams of methyl methacrylate (MMA); 16 grams of ethyl methacrylate (EMA); 10 grams of 2-phenoxyethyl acrylate (SR339 from Sartomer); 7.5 grams of rubber impact modifier S2006 (from Mitsubishi Rayon Co.); 1.0 grams of 2,4,6-trimethylbenzoyldiphenylphosphine oxide, (Lucirin TPO available from BASF); and 0.5 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 8

Dental Materials

A polymerizable dental material was prepared by stirring at ambient temperature a liquid mixture of 30 grams of oligomer made following the procedure of Example 1; 53 grams of methyl methacrylate (MMA); 5 grams of SR368* [Tris(2-Hydroxy Ethyl) Isocyanurate Triacrylate, from Sartomer]; 9 grams of rubber impact modifier S2006 (from Mitsubishi Rayon Co.); 2.0 grams of 2,4,6-trimethylbenzoyldiphenylphosphine oxide, (Lucirin TPO available from BASF); and 1.0 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 9

Dental Materials

The formulation of this example can be used as high strength/toughness sealer to apply on dental devices, which can be cured rapidly without air inhibiting layer. A polymerizable dental material was prepared by stirring at ambient temperature a liquid mixture of 30.0 grams of SR368* [Tris(2-Hydroxy Ethyl) Isocyanurate Triacrylate, from Sartomer]; 52.25 grams of methyl methacrylate (MMA); 9.0 grams of rubber impact modifier S2006 (from Mitsubishi Rayon Co.); 3.5 grams of SR399* (Dipentaerythritol pentaacrylate, from Sartomer); 1.0 gram of BKY-UV 3530 (Polyether modified acryl functional polydimethyl siloxane); 3.5 grams of 2,4,6-trimethylbenzoyldiphenylphosphine oxide (Lucirin TPO available from BASF); 0.75 grams of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 10

Dental Materials

A polymerizable dental material was prepared by stirring at ambient temperature a liquid mixture of 35 grams of oligomer made following the procedure of Example 1; 16 grams of methyl methacrylate (MMA); 20 grams of cyclohexyl methacrylate (CHMA); 20 grams of 2-phenoxyethyl acrylate (SR339 from Sartomer); 7.5 grams of rubber impact modifier S2006 (from Mitsubishi Rayon Co.); 1.0 grams of 2,4,6-trimethylbenzoyldiphenylphosphine oxide, (Lucirin TPO available from BASF); and 0.5 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 11

Dental Materials

A polymerizable dental material was prepared by stirring at ambient temperature a liquid mixture of 35 grams of oligomer made following the procedure of Example 1; 16 grams of ethyl methacrylate (EMA); 20 grams of cyclohexyl methacrylate (CHMA); 20 grams of 2-phenoxyethyl acrylate (SR339 from Sartomer); 7.5 grams of rubber impact modifier S2006 (from Mitsubishi Rayon Co.); 1.0 grams of 2,4,6-trimethylbenzoyldiphenylphosphine oxide, (Lucirin TPO available from BASF); and 0.5 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 12

Dental Materials

A polymerizable dental material was prepared by stirring at ambient temperature a liquid mixture of 35 grams of oligomer made following the procedure of Example 1; 54.5 grams of methyl methacrylate (MMA); 7.5 grams of rubber impact modifier S2006 (from Mitsubishi Rayon Co.); 2.0 grams of 2,4,6-trimethylbenzoyldiphenylphosphine oxide, (Lucirin TPO available from BASF); and 1.0 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 13

Dental Materials

A polymerizable dental material was prepared by stirring at ambient temperature a liquid mixture of 35.0 grams of oligomer made following the procedure of Example 1; 52.0 grams of methyl methacrylate (MMA); 10.0 grams of SR368* [Tris(2-Hydroxy Ethyl) Isocyanurate Triacrylate, from Sartomer]; 2.0 grams of 2,4,6-trimethylbenzoyldiphenylphosphine oxide, (Lucirin TPO available from BASF); and 1.0 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 14

Dental Materials

A polymerizable dental material was prepared by stirring at ambient temperature a liquid mixture of 35.0 grams of oligomer made following the procedure of Example 1; 52.0 grams of methyl methacrylate (MMA); 10.0 grams of ethyleneglycol dimethacrylate (EGDMA); 2.0 grams of 2,4,6-trimethylbenzoyldiphenylphosphine oxide, (Lucirin TPO available from BASF); and 1.0 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

Example 15

Dental Materials

A polymerizable dental material was prepared by stirring at ambient temperature a liquid mixture of 35.0 grams of oligomer made following the procedure of Example 1; 52.0 grams of methyl methacrylate (MMA); 10.0 grams of cyclohexyl methacrylate (CHMA); 2.0 grams of 2,4,6-trimethylbenzoyldiphenylphosphine oxide, (Lucirin TPO available from BASF); and 1.0 gram of visible light initiating solution containing 13.3% camphorquinone (CQ), 23.0% methacrylic acid (MAA), 1.3% butylated hydroxytoluene (BHT), 46% N, N-dimethylaminoethylneopentyl acrylate, and 16.3% γ-methacryloxypropyltrimethoxysilane.

TABLE 1

Mechanical Properties of 30 Printing Formulations

| Material | Stress at Yield (psi) | Modulus (ksi) | Impact Strength Ft-lbs/in$^2$ | Kmax (MPa*m$^{1/2}$) | Work (J/m$^2$) |
|---|---|---|---|---|---|
| Example 5 | — | — | — | 2.87 | 3270 |
| Example 6 | 10,600 | 350 | 8.4 | 2.87 | 2850 |
| Example 7 | — | — | — | 2.84 | 3650 |
| Example 10 | — | — | — | 2.55 | 2160 |
| Example 11 | — | — | — | 2.72 | 3765 |
| Lucitone 199 | 13,800 | 380 | 4.7 | 2.56 | 1550 |

Example 16 (Prophetic)

Advanced SLA Based 3D Printer

A commercially available SLA based 3D printing machine was modified with the laser beam tilted and laser source was modified so as to be able to rotate around the curing chamber.

Example 17 (Prophetic)

Advanced DLP Based 3D Printer

A commercially available DLP based 3D printing machine was modified with the addition of SLA based laser beam tilted toward curing chamber, which was modified so as to be able to rotate around the curing chamber.

Example 18 (Prophetic)

Advanced SLA Based 3D Printer

A commercially available SLA based 3D printing machine was modified with the addition of another SLA based laser beam tilted toward curing chamber, which was modified so as to be able to rotate around the curing chamber.

Example 19 (Prophetic)

Advanced SLA Based 3D Printer

An advanced SLA based 3D printing machine was made with at least one SLA based laser beam tilted toward curing chamber, which is able to rotate around the curing chamber and its intensity and irradiation time is able to be adjusted according to the need for curing different depth. The laser beam intensity and curing time will adjust based on the need for curing depth and the shade of materials.

Example 20 (Prophetic)

Fabrication of Dental Product

The denture base shaded material of Example 5 is made with the addition of pigments and the dentin and enamel shaded materials of Example 13 are made with the addition of pigments. They are loaded into three separate reservoirs. A SLA based 3D printer of Example 16 is used and a laser beam traces out the shape of each layer and hardens the above denture base shaded liquid resin in a layer-wise manner as designed and controlled by a computer to form a denture base or several denture bases. This formed denture base(s) is removed from this denture base bath, and washed and dried. This formed denture base(s) is placed into above prepared dentin shaded liquid resin bath and positioned according to the pre-marked locator and denture design. The tilted laser beam rotates around denture base and traces out the shape of each dentin layer and hardens the above dentin shaded liquid resin in a layer-wise manner as designed and controlled by a computer to form dentin shape on the denture base. Formed denture base(s) with dentin parts of artificial teeth is removed from this bath. After rinsed with solvent and dried, denture base(s) with dentin parts of artificial teeth is immersed into an enamel bath and positioned according to the pre-marked locator and denture design. The tilted laser beam rotates around denture base and traces out the shape of each enamel layer and hardens the above enamel shaded liquid resin in a layer-wise manner as designed and controlled by a computer to form enamel shape on the dentin. Once artificial denture teeth built on the denture base are completed, it is removed from bath, washed and final cured. After polished and finished, the denture(s) is delivered to patient(s). This process can be used to mass manufacture dentures and other dental devices.

Example 21 (Prophetic)

Fabrication of Dental Product

The denture base shaded material of Example 6 is made with the addition of pigments and the dentin shade material of Example 15 and the enamel shaded material of Example 14 are made with the addition of pigments. They are loaded into three separate reservoirs. A DLP/SLA based 3D printer of Example 17 is used and sequential voxel planes are projected into the first denture base liquid resin and harden the above denture base shaded liquid resin in a layer-wise manner as designed and controlled by a computer to form a denture base or several denture bases. This formed denture base(s) is removed from this denture base bath, and washed and dried. This formed denture base(s) is placed into above prepared dentin shaded liquid resin bath and positioned according to the pre-marked locator and denture design. The tilted laser beam of this 3D printer rotates around denture base and traces out the shape of each dentin layer and hardens the above dentin shaded liquid resin in a layer-wise manner as designed and controlled by a computer to form dentin shape on the denture base. Formed denture base(s) with dentin parts of artificial teeth is removed from this bath. After rinsed with solvent and dried, denture base(s) with dentin parts of artificial teeth is immersed into an enamel bath and positioned according to the pre-marked locator and denture design. The tilted laser beam rotates around denture base and traces out the shape of each enamel layer and hardens the above enamel shaded liquid resin in a layer-wise manner as designed and controlled by a computer to form enamel shape on the dentin. Once artificial denture teeth built on the denture base are completed, it is removed from bath, washed and final cured. After polished and finished, the denture(s) is delivered to patient(s). This process can be used to mass manufacture dentures, artificial teeth, crowns and bridges and other dental devices.

Example 22 (Prophetic)

Fabrication of Dental Product

The two dentin and one enamel shaded materials are made with the addition of pigments to formulations of Examples 15 and 14. They are loaded into three separate reservoirs. A SLA based 3D printer of Example 18 is used and two laser beams trace out the shape of each layer in a layer-wise manner as controlled by a computer to form first dentin parts of artificial teeth. Formed first dentin parts of artificial teeth are removed from this bath. After rinsed with solvent and dried, these first dentin parts are immersed into second dentin resin bath and positioned according to the pre-marked locator and denture design. The original laser beam of modified 3D printer and added rotatable tilted laser beam rotating around first dentin parts and trace out the shape of each second dentin layer and harden the above second dentin shaded liquid resin in a layer-wise manner as designed and controlled by a computer to form final dentin shape with two different shades. Formed dentin parts of artificial teeth are removed from this bath. After rinsed with solvent and dried, dentin parts of artificial teeth are immersed into an enamel bath and positioned according to the pre-marked locator. The original laser beam of modified 3D printer and added rotatable tilted laser beam rotating around dentin parts and trace out the shape of each enamel layer and harden the above enamel shaded liquid resin in a layer-wise manner as designed and controlled by a computer to form enamel shape on the dentin parts to obtain final artificial teeth. Finally, artificial teeth are removed from bath, washed and final cured. After polished and finished, these artificial teeth can be used to make dentures and other dental devices. This process can be used to mass manufacture dentures, crowns and bridges and other dental devices.

Example 23 (Prophetic)

Fabrication of Dental Product

The material of Examples 15 is loaded into a reservoir. A denture needed to reline was scanned and immersed into this reservoir with a locator. A SLA based 3D printer of Example 19 is used and laser beam(s) traces out the shape of each layer in a layer-wise manner based on the thickness of every spot especially first layer, where light intensity and irradiation time are varied accordingly to the layer with different thickness at different spots, as controlled by a computer to form relined denture.

Example 24 (Prophetic)

Fabrication of Dental Product

The denture base shaded material of Example 12 is made with the addition of pigments and the dentin shade material of Example 14 and the enamel shaded material of Example 13 are made with the addition of pigments. They are loaded into three separate reservoirs. A SLA based 3D printer of Example 19 is used and laser beam(s) is irradiated into the denture base shaded liquid resin and harden the above denture base shaded liquid resin in a layer-wise manner as designed and controlled by a computer to form a denture base or several denture bases. This formed denture base(s) is removed from this denture base bath, and washed and dried. This formed denture base(s) is placed into above prepared dentin shaded liquid resin bath and positioned according to the pre-marked locator and denture design. The laser beam of this 3D printer traces out the shape of each dentin layer and hardens the above dentin shaded liquid resin in a layer-wise manner as designed and controlled by a computer to form dentin shape on the denture base, based on the thickness of every spot especially the first layer, where light intensity and irradiation time are varied accordingly. A relatively thick first dentin layer may be needed to be adequately cured. Formed denture base(s) with dentin parts of artificial teeth is removed from this bath. After rinsed with solvent and dried, denture base(s) with dentin parts of artificial teeth is immersed into an enamel bath and positioned according to the pre-marked locator and denture design. The laser beam of this 3D printer traces out the shape of each enamel layer and hardens the above enamel shaded liquid resin in a layer-wise manner as designed and controlled by a computer to form enamel shape on the dentin, where light intensity and irradiation time are varied accordingly. Once artificial denture teeth built on the denture base are completed, it is removed from bath, washed and final cured. After polished and finished, the denture(s) is delivered to patient(s). This process can be used to mass manufacture dentures, artificial teeth, crowns and bridges and other dental devices.

The invention claimed is:
1. A method for forming a dental component, the method comprising the steps of:
 (a) providing a carrier and a build plate, said build plate comprising a transparent member, said transparent member comprising a first build surface with said first build surface and said carrier defining a first build region therebetween;
 (b) filling said first build region with a first polymerizable liquid, said first polymerizable liquid contacting said first build surface,
 (c) irradiating said first build region through said build plate to produce a solid polymerized region from said first polymerizable liquid in said first build region;
 (d) advancing said carrier with said first polymerized region adhered thereto away from said first build surface on said build plate to create a subsequent first build region between said polymerized region and said first build surface;
 (e) repeat steps (c) and (d) to form a three-dimensional object having a first surface and a second surface adhered to said carrier, the first surface of the three-dimensional object positioned between the first build surface and a second surface of the three-dimensional object;
 (f) filling a second build region with a second polymerization liquid, wherein an exposed top surface of the second polymerization liquid and a second build surface define the second build region therebetween; and wherein the second polymerizable liquid is different than the first polymerizable liquid;
 (g) repositioning the three-dimensional object so that the first surface of the three-dimensional object is positioned between the exposed top surface of the second polymerizable liquid and the second build surface;
 (h) irradiating the second build region to produce a second solid polymerized region from said second polymerizable liquid in said second build region;
 (i) advancing said carrier with the three-dimensional object and the said second polymerized region adhered the three-dimensional object away from said exposed top surface of the second polymerizable liquid to create a subsequent second build region between said second polymerized region and said second build surface;
 (j) repeat steps (h) and (i) to form said three-dimensional dental component;
 wherein the repositioning step (g), the carrier with the second surface adhered thereto is positioned between the second build surface and the first surface of the three-dimensional object.

2. The method of claim 1, wherein the first surface of the three-dimensional object opposes the second surface of the three-dimensional object.

3. The method of claim 1, wherein the transparent member is a semipermeable member.

4. The method of claim 1, wherein after step (e) and prior to step (f), remaining first polymerizable material is removed from the build plate.

5. The method of claim 4, wherein the filling step (f), the build plate is filled with the second polymerizable material.

6. The method of claim 1, wherein the repositioning step (g), the three-dimensional object in rotated between 135 degrees and 225 degrees.

7. The method of claim 1, wherein the dental component is a denture and the first polymerized region forms part of a denture base of the denture.

8. The method of claim 7, wherein the second polymerized region forms part of a tooth of the denture.

9. The method of claim 1, the first polymerized region has a higher stress yield than the second polymerizable region.

10. The method of claim 1, wherein the carrier is movable from a first position in contact with the exposed top surface of the first polymerizable liquid to a second position elevated above and without contact with the exposed top surface.

11. The method of claim 1, wherein the carrier is movable from a third position within the second polymerizable liquid to a fourth position within the second polymerizable liquid further away from the exposed top surface of the second polymerizable liquid.

12. A method for forming a dental component, the method comprising the steps of:
 (a) providing a carrier and a build plate, said build plate comprising a transparent member, said transparent member comprising a first build surface with said first build surface and said carrier defining a first build region therebetween;
 (b) filling said first build region with a first polymerizable liquid, said first polymerizable liquid contacting said first build surface,
 (c) irradiating said first build region through said build plate to produce a solid polymerized region from said first polymerizable liquid in said first build region;
 (d) advancing said carrier with said first polymerized region adhered thereto away from said first build surface on said build plate to create a subsequent first build region between said polymerized region and said first build surface;
 (e) repeat steps (c) and (d) to form a three-dimensional object having a first surface and a second surface adhered to said carrier, the first surface of the three-dimensional object positioned between the first build surface and a second surface of the three-dimensional object;
 (f) filling a second build region with a second polymerization liquid, wherein an exposed top surface of the second polymerization liquid and a second build surface define the second build region therebetween; and wherein the second polymerizable liquid is different than the first polymerizable liquid;
(g) repositioning the three-dimensional object so that the first surface of the three-dimensional object is positioned between the exposed top surface of the second polymerizable liquid and the second build surface;
(h) irradiating the second build region to produce a second solid polymerized region from said second polymerizable liquid in said second build region;
(i) advancing said carrier with the three-dimensional object and the said second polymerized region adhered the three-dimensional object away from said exposed top surface of the second polymerizable liquid to create a subsequent second build region between said second polymerized region and said second build surface;
(j) repeat steps (h) and (i) to form said three-dimensional dental component;
wherein the repositioning step (g), the three-dimensional object is rotated between 90 degrees and 270 degrees.

13. A method for forming a dental component, the method comprising the steps of:
(a) providing a carrier and a build plate, said build plate comprising a transparent member, said transparent member comprising a first build surface with said first build surface and said carrier defining a first build region therebetween;
(b) filling said first build region with a first polymerizable liquid, said first polymerizable liquid contacting said first build surface,
(c) irradiating said first build region through said build plate to produce a solid polymerized region from said first polymerizable liquid in said first build region;
(d) advancing said carrier with said first polymerized region adhered thereto away from said first build surface on said build plate to create a subsequent first build region between said polymerized region and said first build surface;
(e) repeat steps (c) and (d) to form a three-dimensional object having a first surface and a second surface adhered to said carrier, the first surface of the three-dimensional object positioned between the first build surface and a second surface of the three-dimensional object;
(f) filling a second build region with a second polymerization liquid, wherein an exposed top surface of the second polymerization liquid and a second build surface define the second build region therebetween; and wherein the second polymerizable liquid is different than the first polymerizable liquid;
(g) repositioning the three-dimensional object so that the first surface of the three-dimensional object is positioned between the exposed top surface of the second polymerizable liquid and the second build surface;
(h) irradiating the second build region to produce a second solid polymerized region from said second polymerizable liquid in said second build region;
(i) advancing said carrier with the three-dimensional object and the said second polymerized region adhered the three-dimensional object away from said exposed top surface of the second polymerizable liquid to create a subsequent second build region between said second polymerized region and said second build surface;
(j) repeat steps (h) and (i) to form said three-dimensional dental component;
wherein at least one radiation source is provided for irradiation of steps (c) and/or (h);

wherein the at least one radiation source includes a second radiation source such that the exposed surface of the second polymerizable liquid is provided between the second radiation source and the second build surface.

14. The method of claim 13, wherein the at least one radiation source includes a first radiation source such that the transparent member is provided between the first radiation source and the first build surface.

15. A method for forming a dental component, the method comprising the steps of:
(a) providing a carrier and a build plate, said build plate comprising a transparent member, said transparent member comprising a first build surface with said first build surface and said carrier defining a first build region therebetween;
(b) filling said first build region with a first polymerizable liquid, said first polymerizable liquid contacting said first build surface,
(c) irradiating said first build region through said build plate to produce a solid polymerized region from said first polymerizable liquid in said first build region;
(d) advancing said carrier with said first polymerized region adhered thereto away from said first build surface on said build plate to create a subsequent first build region between said polymerized region and said first build surface;
(e) repeat steps (c) and (d) to form a three-dimensional object having a first surface and a second surface adhered to said carrier, the first surface of the three-dimensional object positioned between the first build surface and a second surface of the three-dimensional object;
(f) filling a second build region with a second polymerization liquid, wherein an exposed top surface of the second polymerization liquid and a second build surface define the second build region therebetween; and wherein the second polymerizable liquid is different than the first polymerizable liquid;
(g) repositioning the three-dimensional object so that the first surface of the three-dimensional object is positioned between the exposed top surface of the second polymerizable liquid and the second build surface;
(h) irradiating the second build region to produce a second solid polymerized region from said second polymerizable liquid in said second build region;
(i) advancing said carrier with the three-dimensional object and the said second polymerized region adhered the three-dimensional object away from said exposed top surface of the second polymerizable liquid to create a subsequent second build region between said second polymerized region and said second build surface;
(j) repeat steps (h) and (i) to form said three-dimensional dental component;
wherein at least one radiation source is provided for irradiation of steps (c) and/or (h);
wherein the at least one radiation source is movable from a first position such the transparent member is provided between the first radiation source and the first build surface and a second position such that the exposed surface of the second polymerizable liquid is provided between the second radiation source and the second build surface.

16. A method for forming a dental component, the method comprising the steps of:
(a) providing a carrier and a build plate, said build plate comprising a transparent member, said transparent member comprising a first build surface with said first build surface and said carrier defining a first build region therebetween;
(b) filling said first build region with a first polymerizable liquid, said first polymerizable liquid contacting said first build surface,
(c) irradiating said first build region through said build plate to produce a solid polymerized region from said first polymerizable liquid in said first build region;
(d) advancing said carrier with said first polymerized region adhered thereto away from said first build surface on said build plate to create a subsequent first build region between said polymerized region and said first build surface;
(e) repeat steps (c) and (d) to form a three-dimensional object having a first surface and a second surface adhered to said carrier, the first surface of the three-dimensional object positioned between the first build surface and a second surface of the three-dimensional object;
(f) filling a second build region with a second polymerization liquid, wherein an exposed top surface of the second polymerization liquid and a second build surface define the second build region therebetween; and wherein the second polymerizable liquid is different than the first polymerizable liquid;
(g) repositioning the three-dimensional object so that the first surface of the three-dimensional object is positioned between the exposed top surface of the second polymerizable liquid and the second build surface;
(h) irradiating the second build region to produce a second solid polymerized region from said second polymerizable liquid in said second build region;
(i) advancing said carrier with the three-dimensional object and the said second polymerized region adhered the three-dimensional object away from said exposed top surface of the second polymerizable liquid to create a subsequent second build region between said second polymerized region and said second build surface;
(j) repeat steps (h) and (i) to form said three-dimensional dental component;
wherein at least one radiation source is provided for irradiation of steps (c) and/or (h);
wherein the at least one radiation source includes a first radiation source for irradiation of step (c) so that the transparent member is provided between the first radiation source and the first build surface and the at least one radiation source includes a second radiation source for the irradiation of step (h) such that the exposed surface of the second polymerizable liquid is provided between the second radiation source and the second build surface.

17. A method for forming a dental component, the method comprising the steps of:
(a) providing a carrier and a build plate, said build plate comprising a transparent member, said transparent member comprising a first build surface with said first build surface and said carrier defining a first build region therebetween;
(b) filling said first build region with a first polymerizable liquid, said first polymerizable liquid contacting said first build surface,
(c) irradiating said first build region through said build plate to produce a solid polymerized region from said first polymerizable liquid in said first build region;
(d) advancing said carrier with said first polymerized region adhered thereto away from said first build surface on said build plate to create a subsequent first build region between said polymerized region and said first build surface;
(e) repeat steps (c) and (d) to form a three-dimensional object having a first surface and a second surface adhered to said carrier, the first surface of the three-dimensional object positioned between the first build surface and a second surface of the three-dimensional object;
(f) filling a second build region with a second polymerization liquid, wherein an exposed top surface of the second polymerization liquid and a second build surface define the second build region therebetween; and wherein the second polymerizable liquid is different than the first polymerizable liquid;
(g) repositioning the three-dimensional object so that the first surface of the three-dimensional object is positioned between the exposed top surface of the second polymerizable liquid and the second build surface;
(h) irradiating the second build region to produce a second solid polymerized region from said second polymerizable liquid in said second build region;
(i) advancing said carrier with the three-dimensional object and the said second polymerized region adhered the three-dimensional object away from said exposed top surface of the second polymerizable liquid to create a subsequent second build region between said second polymerized region and said second build surface;
(j) repeat steps (h) and (i) to form said three-dimensional dental component;
wherein the filling step (f), a second build plate is filled with the second polymerizable material; and
wherein the second build plate includes a bottom surface such that the carrier is advanced towards the bottom surface of the second build plate during step (i).

* * * * *